United States Patent
Kumagai et al.

(10) Patent No.: US 9,791,350 B2
(45) Date of Patent: Oct. 17, 2017

(54) EXHAUST GAS ANALYZER VERIFICATION SYSTEM

(71) Applicant: HORIBA, Ltd., Kyoto (JP)

(72) Inventors: Tatsuki Kumagai, Kyoto (JP); Tetsuji Asami, Kyoto (JP); Yosuke Hisamori, Kyoto (JP)

(73) Assignee: Horiba, Ltd., Kyoto (JP)

( * ) Notice: Subject to any disclaimer, the term of this patent is extended or adjusted under 35 U.S.C. 154(b) by 273 days.

(21) Appl. No.: 14/699,959

(22) Filed: Apr. 29, 2015

(65) Prior Publication Data

US 2015/0316447 A1 Nov. 5, 2015

(30) Foreign Application Priority Data

Apr. 30, 2014 (JP) ................................. 2014-094331

(51) Int. Cl.
*G01M 15/10* (2006.01)
*G05D 7/06* (2006.01)
(Continued)

(52) U.S. Cl.
CPC ........ *G01M 15/102* (2013.01); *G01N 1/2252* (2013.01); *G01N 33/0018* (2013.01); *G05D 7/0641* (2013.01); *G01N 2001/2255* (2013.01)

(58) Field of Classification Search
CPC .............. G01M 15/102; G01N 1/2252; G01N 2001/2255; G01N 33/0018; G01N 33/0006; G05D 7/0641; G05D 7/0652
See application file for complete search history.

(56) References Cited

U.S. PATENT DOCUMENTS 4,823,591 A * 4/1989 Lewis ................... G01F 25/003
                                                    73/1.26
5,739,413 A * 4/1998 Kohn .................. G01M 15/102
                                                    73/23.31
(Continued)

FOREIGN PATENT DOCUMENTS

DE    19604417 C1    9/1997
EP     1106983 A2    6/2001
EP     2515095 A1    6/2011

OTHER PUBLICATIONS

Extended European Search Report dated Mar. 21, 2016 issued in European patent application No. 15001246.6, 10 pages.
(Continued)

*Primary Examiner* — Natalie Huls
(74) *Attorney, Agent, or Firm* — Brooks Kushman P.C.

(57) ABSTRACT

A verification system includes a reference gas supply part that supplies reference gas in place of exhaust gas and is configured to be able to verify the consistency between a supply amount of the reference gas from the reference gas supply part and a measured value of the reference gas measured by an analyzer. The verification system further includes a control part that receives a setting flow rate signal that is a signal indicating a setting flow rate and an analysis range signal that is a signal indicating an analysis range of the analyzer, calculates a target supply amount of the reference gas on the basis of the setting flow rate and the analysis range indicated by the respective signals, and controls the reference gas supply part so as to make the reference gas supply amount by the reference gas supply part equal to the target supply amount.

8 Claims, 2 Drawing Sheets

(51) Int. Cl.
   *G01N 33/00* (2006.01)
   *G01N 1/22* (2006.01)

(56) References Cited

U.S. PATENT DOCUMENTS

| | | | | |
|---|---|---|---|---|
| 6,200,819 | B1 * | 3/2001 | Harvey | G01N 1/2252 |
| | | | | 422/83 |
| 6,505,524 | B1 * | 1/2003 | Silvis | G01N 1/2252 |
| | | | | 73/863.03 |
| 6,729,195 | B2 * | 5/2004 | Graze, Jr. | G01N 1/38 |
| | | | | 73/863.03 |
| 9,223,318 | B2 * | 12/2015 | Takeuchi | G05D 7/0652 |
| 9,389,152 | B2 * | 7/2016 | Kumagai | G01N 1/2252 |
| 2001/0013245 | A1 * | 8/2001 | Hanashiro | G01F 1/44 |
| | | | | 73/23.31 |
| 2006/0000256 | A1 * | 1/2006 | Orr | G01N 1/2247 |
| | | | | 73/1.16 |
| 2016/0348561 | A1 * | 12/2016 | Higashi | F01N 3/04 |

OTHER PUBLICATIONS

Engine Emission Measurement Handbook, p. 27-28 Horiba Ltd., Apr. 30, 2013.

* cited by examiner

EXHAUST GAS ANALYZER VERIFICATION SYSTEM

CROSS-REFERENCE TO RELATED APPLICATION

This application claims priority to JP Application No. 2014-094331, filed Apr. 30, 2014, the disclosure of which is incorporated in its entirety by reference herein.

TECHNICAL FIELD

The present invention relates to a verification system used to verify an exhaust gas analysis system adapted to analyze exhaust gas.

BACKGROUND ART

As an exhaust gas analysis system adapted to analyze exhaust gas, there has been known a system that includes an exhaust gas dilution device adapted to dilute exhaust gas with diluent gas and an analyzer adapted to measure components contained in the diluted exhaust gas produced by the exhaust gas dilution device.

More specifically, as the exhaust gas dilution device, a device adapted to control a flow rate of the diluted exhaust gas to a constant flow rate (hereinafter also referred to as a setting flow rate) is used, such as a constant flow rate dilution sampling device, and by changing the setting flow rate, a ratio in flow rate between the exhaust gas and the diluent gas, i.e., a dilution ratio can be changed.

As the analyzer, an analyzer configured to be able to change an analysis range in order to analyze exhaust gases diluted at various dilution ratios by the above-described exhaust gas dilution device is used.

The above-described configuration enables the exhaust gas to be analyzed in accordance with each set of various analysis conditions such as a model of a vehicle and a driving mode by changing the setting flow rate and the analysis range.

Meanwhile, in general, in order to ensure analysis accuracy in this sort of exhaust gas analysis system, the analysis accuracy is verified using predetermined reference gas before analyzing exhaust gas.

As a method for the verification, there is known a method called a propane shot described in, for example, Engine emission measurement handbook, pp. 27 to 28, in which specifically, propane gas having known density is supplied to an exhaust gas analysis system in place of exhaust gas to evaluate the recovery rate of the propane gas.

In the above-described verification, for example, in order to analyze the concentration of propane gas within an analysis range preset in an analyzer, it is necessary to dilute the propane gas at an appropriate dilution ratio, and to do this, a supply flow rate of the propane gas should be appropriately set on the basis of a setting flow rate and the analysis range.

However, since the setting flow rate and the analysis range are ones that are appropriately changed in accordance with a set of analysis conditions as described above, to ensure analysis accuracy in any of various sets of analysis conditions, the propane shot should be performed at a different supply flow rate for each of many combinations obtained by multiplying the number of setting flow rates and the number of analysis ranges by each other, requiring a great amount of time and effort.

The above-described problem is common to exhaust gas analysis systems including an exhaust gas dilution device adapted to dilute exhaust gas to produce diluted exhaust gas, such as a bag mini-diluter in addition to a constant flow rate sampling device, and an analyzer adapted to measure components contained in the diluted exhaust gas.

SUMMARY OF INVENTION

Technical Problem

Therefore, the present invention is made in order to solve the above-described problem, and a main intended object thereof is to make it possible to verify an exhaust gas analysis system without requiring time and effort.

Solution to Problem

That is, a verification system according to the present invention is one that is used to verify the above-described exhaust gas analysis system, and includes a reference gas supply part adapted to supply reference gas in place of exhaust gas. In addition, the verification system is configured to be able to verify the consistency between a reference gas supply amount from the reference gas supply part and a reference gas measured value measured by an analyzer, and further includes a control part that receives a setting flow rate signal that is a signal indicating a setting flow rate of an exhaust gas dilution device and an analysis range signal that is a signal indicating an analysis range of the analyzer, calculates a target supply amount of the reference gas on the basis of the setting flow rate and the analysis range indicated by the respective signals, and controls the reference gas supply part so as to make the reference gas supply amount by the reference gas supply part equal to the target supply amount.

In such a verification system, since the control part calculates the target supply amount on the basis of the setting flow rate and the analysis range, and controls the reference gas supply part so as to make the reference gas supply amount equal to the target supply amount, the reference gas supply amount can be automatically made to correspond to a flow rate suitable for the verification.

In doing so, for each combination of a setting flow rate and an analysis range, the reference gas supply amount can be automatically set, and therefore the exhaust gas analysis system can be verified without requiring time and effort.

Preferably, the reference gas supply part includes: a critical flow orifice provided in a reference gas flow path through which the reference gas flows; and a pressure regulator that is provided upstream of the critical flow orifice in the reference gas flow path and controls the pressure of the reference gas, and the control part controls the pressure regulator so as to make the reference gas supply amount by the reference gas supply part equal to the target supply amount.

In this case, the reference gas supply amount is determined by an aperture size of the critical flow orifice and the pressure of the reference gas, and the control part controls the pressure regulator. As a result, the reference gas supply amount can be automatically set to the target supply amount.

Preferably, the reference gas supply part includes: multiple critical flow orifices that are provided in parallel to a reference gas flow path through which the reference gas flows and have mutually different aperture sizes; and multiple on/off valves that are provided upstream of the respective critical flow orifices in the reference gas flow path, and the control part selectively flows the reference gas to one or more critical flow orifices among the multiple critical flow orifices to make the reference gas supply amount equal to the target supply amount by controlling an on/off state of each of the on/off valves.

In this case, a supply flow rate is determined by an aperture size of a critical flow orifice and the pressure of the reference gas. As a result, since the control part controls each of the on/off valves to selectively flow the reference gas to one or more critical flow orifices, the reference gas supply amount can be automatically set to the target supply amount.

Specific embodiments for verifying the exhaust gas analysis system include an embodiment further including an analysis accuracy detection part that detects the analysis accuracy of the exhaust gas analysis system by comparing supply mass obtained using the density of the reference gas, a supply flow rate of the reference gas, a supply time of the reference gas as parameters and measured mass obtained using the concentration of the reference gas measured by the analyzer, the setting flow rate, and the supply time as parameters.

Specific embodiments of the respective gases include an embodiment where the diluent gas is air, and the reference gas is propane gas.

Embodiments making the effect of the present invention obvious includes an embodiment where the exhaust gas analysis system includes a constant flow rate dilution sampling device.

A reference gas supply part according to the present invention is one that is used for an exhaust gas analysis system including: an exhaust gas dilution device adapted to mix exhaust gas and diluent gas to produce diluted exhaust gas having a predetermined setting flow rate; and an analyzer adapted to measure a component contained in the diluted exhaust gas. In addition, the reference gas supply part is a component part of a verification system configured to be able to verify the consistency between a supply amount of reference gas supplied in place of the exhaust gas and a measured value of the reference gas measured by the analyzer. Further, the reference gas supply part supplies the reference gas so as to meet a target supply amount on the basis of a control signal from a control part that receives a setting flow rate signal that is a signal indicating the setting flow rate and an analysis range signal that is a signal indicating an analysis range of the analyzer and calculates the target supply amount of the reference gas on the basis of the setting flow rate and the analysis range indicated by the respective signals.

In addition, a verification program according to the present invention is a verification program applied to a verification system that is used for an exhaust gas analysis system including: an exhaust gas dilution device adapted to mix exhaust gas and diluent gas to produce diluted exhaust gas having a predetermined setting flow rate; and an analyzer adapted to measure a component contained in the diluted exhaust gas, and configured to be able to verify the consistency between a supply amount of reference gas supplied in place of the exhaust gas and a measured value of the reference gas measured by the analyzer. In addition, the verification program instructs a computer to fulfill a function of a control part that receives a setting flow rate signal that is a signal indicating the setting flow rate and an analysis range signal that is a signal indicating an analysis range of the analyzer, calculates a target supply amount of the reference gas on the basis of the setting flow rate and the analysis range indicated by the respective signals, and performs control so as to make the supply amount of the reference gas equal to the target supply amount.

The reference gas supply part and the verification program as described make it possible to obtain the same working effect as that of the above-described verification system.

Advantageous Effects of Invention

The present invention configured as described can automate the verification of an exhaust gas analysis system, and reduce time and effort necessary to verify the exhaust gas analysis system.

DESCRIPTION OF EMBODIMENTS

In the following, an exhaust gas analysis system 100 using a verification system 200 according to the present invention will be described with reference to the drawings.

The exhaust gas analysis system 100 according to the present invention is one of a dilution sampling type, and dilutes exhaust gas, which is emitted from an internal combustion engine such as an engine, several times with diluent gas purified from air to perform concentration measurement using an exhaust gas dilution device. In the present embodiment, as the exhaust gas dilution device, a constant flow rate dilution sampling device 101 that samples a total amount of exhaust gas and dilutes the exhaust gas with diluent gas to control a flow rate of the diluted exhaust gas to a constant flow rate (hereinafter also referred to as a setting flow rate) will be described below.

Figure 1:
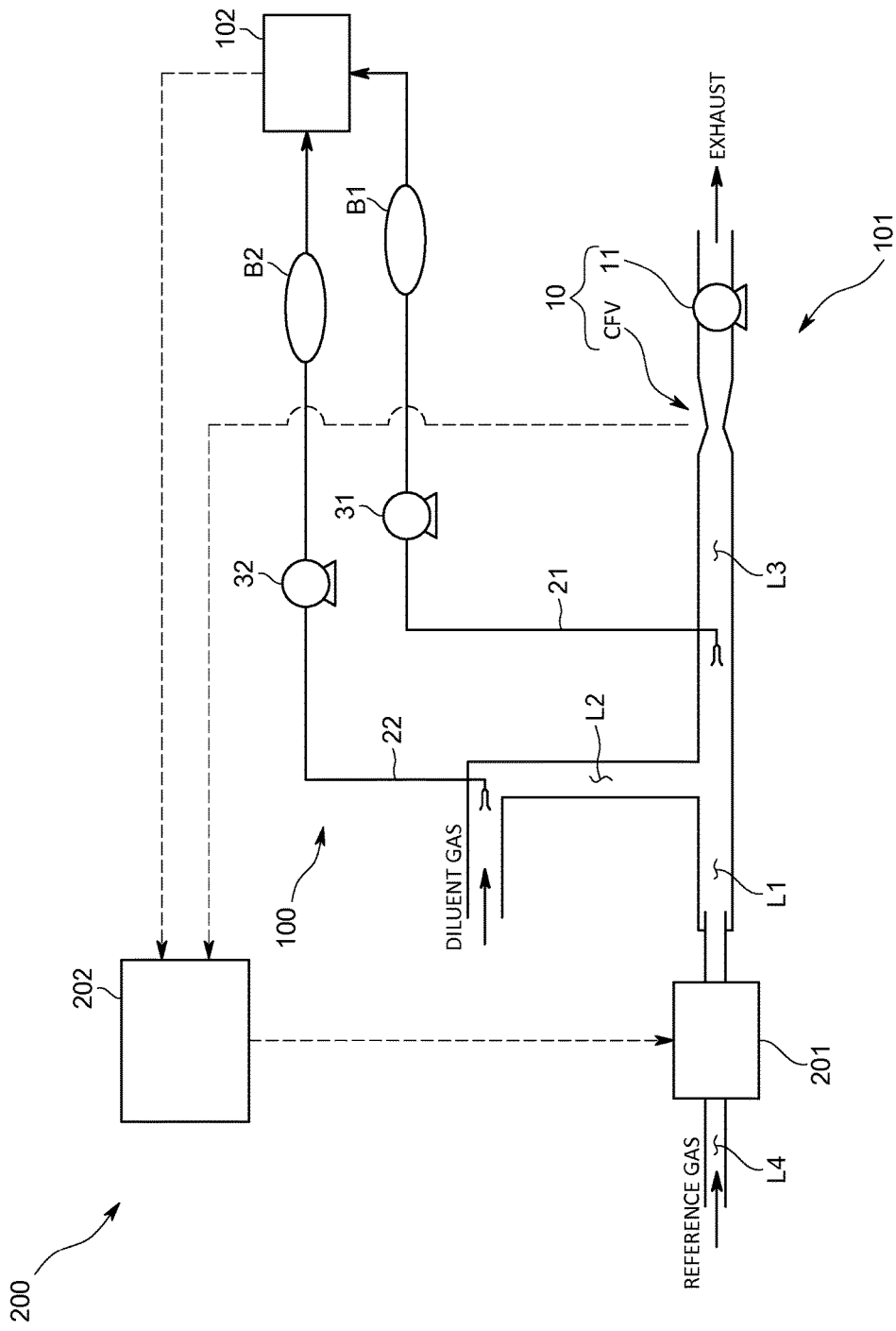
FIG. 1 is a general view schematically illustrating a configuration of a verification system in the present embodiment.

Specifically, as illustrated in FIG. 1, the exhaust gas analysis system 100 includes: the constant flow rate dilution sampling device 101 that constantly controls a total flow rate of a total amount of the exhaust gas and the diluent gas to the setting flow rate, and samples part of the diluted exhaust gas and part of the diluent gas; a diluted exhaust gas sampling bag B1 that contains the sampled diluted exhaust gas; a diluent gas sampling bag B2 that contains the sampled diluent gas; and an analyzer 102 that analyzes the concentrations of a predetermined component (such as HC, CO, or CO2) in the sampled gases in the respective sampling bags B1 and B2.

As illustrated in FIG. 1, the constant flow rate dilution sampling device 101 includes: an exhaust gas flow path L1 into which the exhaust gas emitted from, for example, an unillustrated internal combustion engine is introduced; a diluent gas flow path L2 that meets the exhaust gas flow path L1, through which the diluent gas flows; and a main flow path L3 having a constant flow rate mechanism 10 that is provided downstream of the meeting point between the exhaust gas flow path L1 and the diluent gas flow path L2, and makes the flow rate of the diluted exhaust gas constant.

Note that the diluent gas in the present embodiment is air purified by, for example, an unillustrated air purification device.

The constant flow rate mechanism 10 is, as illustrated in FIG. 1, of a critical flow venturi type including a critical flow venturi CFV and a suction blower 11. The constant flow rate mechanism 10 in the present invention includes multiple critical flow venturis CFV provided in parallel, and is configured to, in accordance with a setting flow rate signal, for example, an operator inputs using input means (such as a keyboard and a mouse), automatically switch to a critical flow venturis CFV where the diluted exhaust gas is to flow. Specifically, unillustrated on/off valves or the like receive the setting flow rate signal, then on/off states of the valves are changed to change to a critical flow venturi CFV automatically where the diluted exhaust gas is to flow, and consequently the setting flow rate, i.e., the flow rate of the diluted exhaust gas is changed. Alternatively, the constant flow rate mechanism 10 may be configured to be able to manually replace a critical flow venturi CFV.

Note that FIG. 1 illustrates only one predetermined critical flow venturi CFV.

In addition, the suction blower 11 may be replaced by a suction pump.

As illustrated in FIG. 1, the above-described constant flow rate dilution sampling device 101 further includes: a diluted exhaust gas sampling pipe 21 for partially sampling the diluted exhaust gas from the main flow path L3; and a diluent gas sampling pipe 22 for partially sampling the diluent gas from the diluent gas flow path L2.

Specifically, the diluted exhaust gas sampling pipe 21 is a pipe of which one end is provided inside the main flow path L3 and the other end is connected to the diluted exhaust gas sampling bag B1. The diluted exhaust gas sampling pipe 21 is provided with a diluted exhaust gas sampling pump 31.

Note that the diluted exhaust gas sampling pipe 21 is provided on the upstream side of the constant flow rate mechanism 10.

On the other hand, the diluent gas sampling pipe 22 is a pipe of which one end is provided inside the diluent gas flow path L2 and the other end is connected to the diluent gas sampling bag B2. The diluent gas sampling pipe 22 is provided with a diluent gas sampling pump 32.

The analyzer 102 is one that measures the concentrations of the predetermined component in the gases sampled in the respective sampling bags B1 and B2, and in the present embodiment, a THC meter adapted to measure the concentration of THC using a hydrogen flame ionization detecting method (FID).

The analyzer 102 is configured to change an analysis range in such a way that an operator inputs a desired analysis range to, for example, an unillustrated host computer controlling the analyzer 102. The present embodiment is configured such that an operator selects one from among, for example, nine different analysis ranges.

Note that the analyzer 102 may be an NOx meter that measures the concentration of NOx using a chemiluminescence method (CLD), an infrared gas analyzer that measures the concentrations of components such as HC, CO, and CO2 using a non-dispersive infrared absorption method (NDIR), O2 meter that measures the concentration of O2 using a magnetic pressure method (PMD), or a CH4 meter that measures the concentration of CH4 using a gas chromatograph/hydrogen flame ionization detector (GC-FID).

The verification system 200 used for the exhaust gas analysis system 100 configured as described is a system adapted to verify the analysis accuracy of the exhaust gas analysis system 100, and specifically, configured to be able to supply reference gas having known components in place of exhaust gas, and verify the consistency between a supply amount of the supplied reference gas and a measured value of the reference gas measured by the analyzer 102.

The verification system 200 of the present embodiment employs a method referred to as a so-called propane shot method. Also, the verification system 200 is connected to the exhaust gas analysis system 100 and configured to be able to verify the analysis accuracy of the exhaust gas analysis system 100 by supplying propane gas having known density to the exhaust gas analysis system 100 as the reference gas and evaluating the recovery rate of the reference gas.

More specifically, the verification system 200 is configured to supply the propane gas to the constant flow rate dilution sampling device 101 through the exhaust gas flow path L1, calculate supply mass Min corresponding to a supply amount of the propane gas actually supplied, and measured mass Mout corresponding to a measured value obtained by the analyzer 102 measuring propane gas recovered in the diluted exhaust gas sampling bag B1, on the basis of the following expressions (1) and (2), and compare these values with each other.

$$M_{in} = \rho \times q \times t \tag{1}$$

$$M_{out} = (Cs - Ca) \times Q \times t \tag{2}$$

Here, $\rho$ is the density of propane gas, q is a supply flow rate of the propane gas, t is a supply time of the propane gas, Cs is the concentration of HC in the diluted exhaust gas sampling bag B1 obtained by the analyzer 102, Ca is the concentration of HC in the diluent gas sampling bag B2 obtained by the analyzer 102, and Q is the flow rate of the constant flow rate dilution sampling device 101.

Next, a specific configuration of the verification system 200 is described.

As illustrated in FIG. 1, the verification system 200 includes: a reference gas flow path L4 of which one end is connected to the exhaust gas flow path L1 and the other end is connected to, for example, an unillustrated gas cylinder, through which the reference gas flows, which is propane gas sent from the gas cylinder; a reference gas supply part 201 that is provided in the reference gas flow path L4 and supplies the reference gas to the exhaust gas flow path L1; and a control device 202 as a control part that transmits a control signal to the reference gas supply part 201 to control a supply flow rate of the reference gas.

Figure 2:
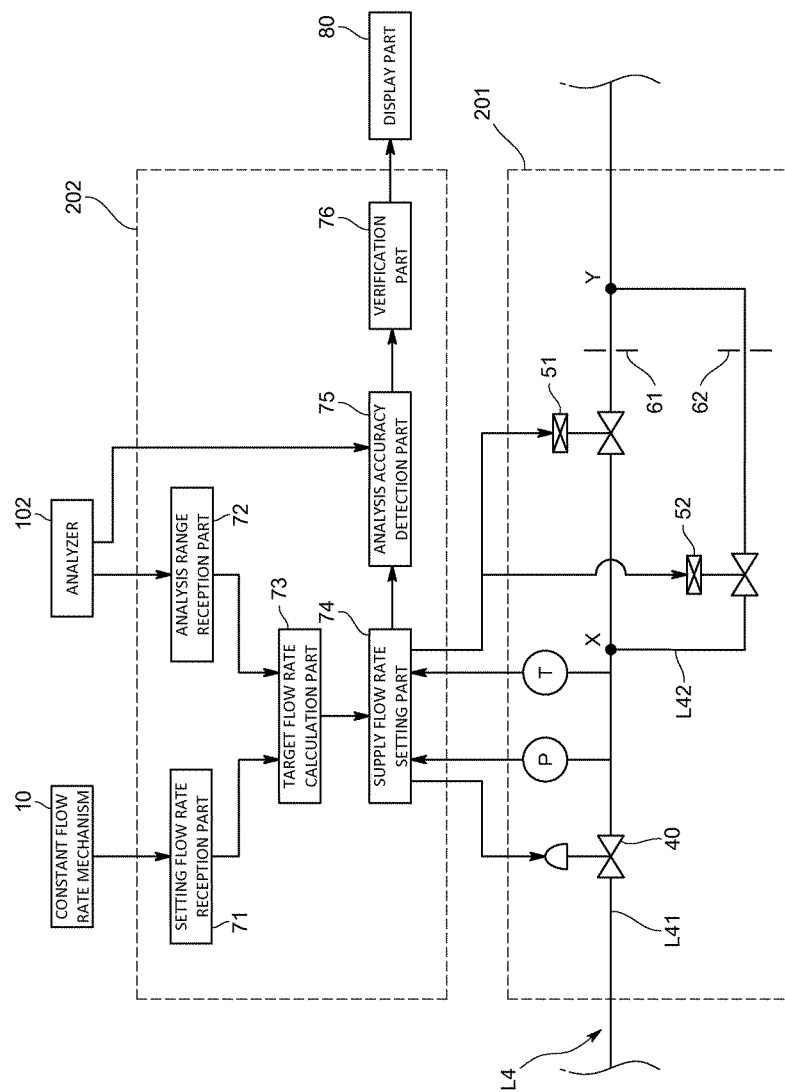
FIG. 2 is a diagram schematically illustrating a configuration of a reference gas supply part in the same embodiment.

As illustrated in FIG. 2, the reference gas flow path L4 includes; a main flow path L41 that is connected to the unillustrated gas cylinder; and a branching flow path L42 that branches from a branching point X in the main flow path L41 and meets the main flow path L41 at a meeting point Y in the main flow path L41.

As illustrated in FIG. 2, the reference gas supply part 201 includes: a pressure regulator 40 that is provided upstream of the branching point X in the main flow path L41 and regulates the pressure of the fluid flowing through the main flow path L41; a pressure gauge P adapted to measure the pressure of the fluid and a thermometer T adapted to measure the temperature of the fluid; a first on/off valve 51 and a first critical flow orifice 61 that are provided between the branching point X and the meeting point Y in the main flow path L41; and a second on/off valve 52 and a second critical flow orifice 62 that are provided in the branching flow path L42.

The critical flow orifices 61 and 62 in the present embodiment are ones having mutually different aperture sizes, and provided in parallel to the reference gas flow path L4.

The respective on/off valves 51 and 52 are solenoid valves provided upstream of the corresponding critical flow orifices 61 and 62, respectively.

Since the above-described critical flow orifices 61 and 62 and on/off valves 51 and 52 are provided, the reference gas supply part 201 can selectively flow the reference gas to any one of the critical flow orifices 61 and 62 by switching an on/off state between the on/off valves 51 and 52.

The above-described configuration allows the supply flow rate of the reference gas supplied from the reference gas supply part 201 to be determined by the pressure of the reference gas (hereinafter also referred to as reference gas pressure) regulated by the pressure regulator 40, and the aperture size of a critical flow orifice 61 or 62 through which the reference gas flows.

Further, the verification system 200 according to the present embodiment is configured such that the control signal is sent from the control device 202 to the reference gas supply part 201 in order to automatically set the above-described supply flow rate of the reference gas.

The control device 202 is described below.

The control device 202 is one that controls the supply amount of the reference gas such that a reference gas analysis result by the analyzer 102 falls within an analysis range set in the analyzer 102.

Specifically, the control device 202 includes a CPU, a memory, an A/D converter, a D/A converter, and the like. In addition, the CPU and its peripheral devices cooperates, and thereby as illustrated in FIG. 2, the control device 202 fulfils functions as a setting flow rate reception part 71, an analysis range reception part 72, a target flow rate calculation part 73, a supply flow rate setting part 74, an analysis accuracy detection part 75, and a verification part 76.

The setting flow rate reception part 71 is one that receives a setting flow rate signal, which is a signal indicating the setting flow rate, from the constant flow rate mechanism 10 provided in the above-described constant flow rate dilution sampling device 101.

The analysis range reception part 72 is one that from the analyzer 102, obtains an analysis range signal, which is a signal indicating an analysis range set by, for example, an operator from among the multiple analysis ranges.

The target flow rate calculation part 73 is one that obtains the setting flow rate and the analysis range from the setting flow rate reception part 71 and the analysis range reception part 72, respectively, to calculate a target flow rate corresponding to a target supply amount of the reference gas using the setting flow rate and the analysis range as parameters, as well as transmitting a target flow rate signal indicating the calculated target flow rate to the below-described supply flow rate setting part 74.

More specifically, the target flow rate calculation part 73 is configured to calculate the target flow rate on the basis of the following expression (3).

$$q = Q \times kR \quad (3)$$

Here, q is the target flow rate, Q the setting flow rate, k a proportionality factor, and R the analysis range. Note that k can be arbitrarily set, and in the present embodiment, k is 0.8.

The supply flow rate setting part 74 is one that receives the target flow rate signal transmitted by the target flow rate calculation part 73 to transmit the control signal to the above-described reference gas supply part 201, and thereby sets the supply flow rate to the target flow rate.

More specifically, as illustrated in FIG. 2, the supply flow rate setting part 74 obtains measured pressure and measured temperature respectively by the above-described pressure gauge P and thermometer T together with the target flow rate, and uses the following expression (4) to calculate the reference gas pressure on the basis of the target flow rate and the measured temperature.

$$q = (A_0 + A_1 \times P + A_2 \times P^2)/T^{1/2} \quad (4)$$

Here, q is the target flow rate, $A_0$ to $A_2$ orifice calibration factors, P the reference gas pressure, and T the measured temperature.

In the present embodiment, the supply flow rate setting part 74 is configured to control the reference gas pressure by performing, for example, feedback control using the measured pressure, and also send the control signal to the pressure regulator 40, the first on/off valve 51, and the second on/off valve 52.

More specifically, on the basis of the above-described control signal, the pressure regulator 40 regulates the pressure inside the reference gas flow path L4 to the reference gas pressure determined by the supply flow rate setting part 74, and the respective on/off valves 51 and 52 switch the on/off state such that the reference gas flows through a critical flow orifice 61 or 62 selected by the supply flow rate setting part 74.

In doing so, the supply flow rate is automatically set to the target flow rate.

The analysis accuracy detection part 75 is one that compares supply data obtained using the supply flow rate set by the supply flow rate setting part 74 as a parameter and measurement data obtained using the concentrations of the reference gas in the sampling bags B1 and B2 measured by the analyzer 102 as parameters to detect analysis accuracy.

The analysis accuracy detection part 75 in the present embodiment is configured to, on the basis of the above-described expressions (1) and (2), calculate the supply mass $M_{in}$ of the reference gas and the measured mass $M_{out}$ obtained by measuring the reference gas recovered in the sampling bags B1 and B2, and detect, for example, a ratio between the supply mass $M_{in}$ and the measured mass $M_{out}$ as the analysis accuracy.

The verification part 76 is one that verifies whether or not the analysis accuracy detected by the analysis accuracy detecting part 75 is within an allowable error range.

Specifically, the verification part 76 calculates an accuracy error z on the basis of the following expression (5), verifies whether or not the accuracy error z is within, for example, ±2% or ±3%, and displays a result of the verification on a display part 80 such as a display.

$$z = (M\text{out} + M\text{in}) \times 100 - 100 \quad (5)$$

Since the control device 202 automatically sets the supply flow rate of the reference gas to the target flow rate on the basis of a setting flow rate of the constant flow rate dilution sampling device 101 and an analysis range of the analyzer 102, the verification system 200 according to the present embodiment configured as described can detect the analysis accuracy of the exhaust gas analysis system 100 for each combination of a setting flow rate and an analysis range without requiring time and effort.

Also, since analysis accuracy can be detected as described above, by verifying whether or not the analysis accuracy is within the allowable error range, the whole of the exhaust gas analysis system 100 including the constant flow rate dilution sampling device 101 and the analyzer 102 can be verified.

In addition, in the case where the analysis accuracy is out of the allowable error range, it is necessary to inspect the exhaust gas analysis system 100. Possible main causes in this case include the accuracy of a setting flow rate set in the constant flow rate dilution sampling device 101, failure of analyzer 102, fluid leakage in the system, failure in mixture at any of the sampling points or any of the sampling bags, accuracy at the time of reference gas injection, supply mass calculation error, and the like.

Further, even in the case where the target flow rate is widely changed in accordance with various sets of analysis conditions, when setting the supply flow rate to the target flow rate, the supply flow rate setting part 74 can perform the setting using the two parameters, i.e., the reference gas pressure and the aperture size of a critical flow orifice 61 or 62, and can therefore surely set the supply flow rate to the target flow rate.

In addition, the verification part 76 verifies a detection result by the analysis accuracy detection part 75 to display the detection result on the display part 80, and therefore almost all steps of verifying the whole of the exhaust gas analysis system 100 can be automated.

Note that the present invention is not limited to the above-described embodiment.

For example, in the above-described embodiment, the exhaust gas dilution device is the constant flow rate dilution sampling device, but alternatively may be a bag mini-diluter.

Also, in the above-described embodiment, the two critical flow orifices are provided in parallel, but three or more critical flow orifices may be provided in parallel.

Further, the setting flow rate reception part in the above-described embodiment receives the setting flow rate of the constant flow rate dilution sampling device, but may be one that receives, for example, a characteristic value related to a critical flow venturi selected from among multiple critical flow venturis, such as a calibration factor, and calculates the setting flow rate using the characteristic value as a parameter.

In addition, the setting flow rate reception part and the analysis range reception part may be ones that as the setting flow rate signal and the analysis range signal, respectively, receive a setting flow rate and an analysis range inputted by, for example, an operator using input means such as a keyboard.

Also, the analysis accuracy detection part in the above-described embodiment is configured to detect the analysis accuracy by comparing the supply mass and measured mass of the reference gas, but may be configured to detect the analysis accuracy by comparing various physical quantities, such as comparing supply mass per unit time and measured mass per unit time, or comparing the density of the reference gas and the measured concentration of the reference gas measured by the analyzer.

Further, the supply flow rate setting part in the above-described embodiment uses the predetermined calculating expression to calculate the reference gas pressure on the basis of the target flow rate and the measured temperature, but may be configured to refer to, for example, a lookup table stored in a predetermined area of the memory to determine the reference gas pressure and the aperture size of a critical flow orifice on the basis of the target flow rate and the measured temperature.

Still further, it is not necessary that the analysis accuracy detection part and the verification part are functional parts of the control device as in the above-described embodiment, but the analysis accuracy detection part and the verification part may be functional parts of a device different from the control device, such as an arithmetic device.

Yet further, the reference gas in the above-described embodiment is propane gas, but may be another gas having known components and density, or gas containing calibration particles.

Also, the exhaust gas analysis system in the above-described embodiment is one having the sampling bags, but may be a system that, for example, performs continuous analysis without using any sampling bag.

Besides, it should be appreciated that the present invention is not limited to any of the above-described embodiments, but can be variously modified without departing from the scope thereof.

REFERENCE SIGNS LIST

100: Exhaust gas analysis system
200: Verification system
101: Constant flow rate dilution sampling device
102: Analyzer
10: Constant flow rate mechanism
CFV: Critical flow venturi
201: Reference gas supply part
202: Control device
40: Pressure regulator
51: First on/off valve
61: First critical flow orifice
52: Second on/off valve
62: Second critical flow orifice

What is claimed is:

1. A verification system used for an exhaust gas analysis system including an exhaust gas dilution device that mixes exhaust gas and diluent gas to produce diluted exhaust gas having a predetermined setting flow rate, and an analyzer that measures a component contained in the diluted exhaust gas, the verification system comprising:
    a reference gas supply part adapted to supply reference gas in place of the exhaust gas;
    a flow rate reception part that receives a setting flow rate signal that is a signal indicating the setting flow rate;
    an analysis range reception part that receives an analysis range signal that is a signal indicating an analysis range of the analyzer;
    a target flow rate calculation part that calculates a target supply amount of the reference gas on a basis of the setting flow rate and the analysis range indicated by the respective signals; and
    a supply flow rate setting part that controls the reference gas supply part and makes a reference gas supply amount by the reference gas supply part equal to the target supply amount.

2. The verification system according to claim 1, wherein the reference gas supply part comprises:
    a critical flow orifice provided in a reference gas flow path through which the reference gas flows,
    a pressure regulator that is provided upstream of the critical flow orifice in the reference gas flow path and controls pressure of the reference gas, and
    the supply flow rate setting part controls the pressure regulator so as to make the reference gas supply amount by the reference gas supply part equal to the target supply amount.

3. The verification system according to claim 1, wherein the reference gas supply part comprises:
    multiple critical flow orifices that are provided in parallel to a reference gas flow path through which the reference gas flows and have mutually different aperture sizes, multiple on/off valves that are provided upstream of the respective critical flow orifices in the reference gas flow path, and the supply flow rate setting part selectively flows the reference gas to one or more critical flow orifices among the multiple critical flow orifices to make the reference gas supply amount equal to the target supply amount by controlling an on/off state of each of the on/off valves.

4. The verification system according to claim 1, further comprising an analysis accuracy detection part that detects analysis accuracy of the exhaust gas analysis system by comparing supply mass obtained using density of the reference gas, a supply flow rate of the reference gas, a supply time of the reference gas as parameters and measured mass obtained using concentration of the reference gas, the concentration being measured by the analyzer, the setting flow rate, and the supply time as parameters.

5. The verification system according to claim 1, wherein the diluent gas is air, and the reference gas is propane gas.

6. The verification system according to claim 1, wherein the exhaust gas analysis system comprises a constant flow rate dilution sampling device.

7. A control device that is used for an exhaust gas analysis system including: an exhaust gas dilution device adapted to mix exhaust gas and diluent gas to produce diluted exhaust gas having a predetermined setting flow rate, and an analyzer adapted to measure a component contained in the diluted exhaust gas, the control device comprising:

a flow rate reception part that receives a setting flow rate signal that is a signal indicating the setting flow rate;

an analysis range reception part that receives an analysis range signal that is a signal indicating an analysis range of the analyzer;

a target flow rate calculation part that calculates a target supply amount of a reference gas on a basis of the setting flow rate and the analysis range indicated by the respective signals; and a supply flow rate setting part that controls a reference gas supply part and makes a reference gas supply amount by the reference gas supply part equal to the target supply amount.

8. A method of controlling a verification system used for an exhaust gas analysis system including an exhaust gas dilution device adapted to mix exhaust gas and diluent gas to produce diluted exhaust gas having a predetermined setting flow rate, and an analyzer adapted to measure a component contained in the diluted exhaust gas, the method comprising:

by a control device,
receiving a setting flow rate signal that is a signal indicating the setting flow rate,
receiving an analysis range signal that is a signal indicating an analysis range of the analyzer,
calculating a target supply amount of a reference gas on a basis of the setting flow rate and the analysis range indicated by the respective signals, and
controlling a reference gas supply part and making a reference gas supply amount by the reference gas supply part equal to the target supply amount.

\* \* \* \* \*